United States Patent [19]

Collins et al.

[11] Patent Number: 4,689,754
[45] Date of Patent: Aug. 25, 1987

[54] OPTIMIZATION APPARATUS AND PROCEDURE

[75] Inventors: John B. Collins, Westport; George E. Kisslak, Huntington, both of Conn.

[73] Assignee: The Perkin-Elmer Corporation, Norwalk, Conn.

[21] Appl. No.: 704,358

[22] Filed: Feb. 21, 1985

[51] Int. Cl.⁴ .............................................. G06F 15/20
[52] U.S. Cl. .................................. 364/497; 364/577; 364/578
[58] Field of Search ............... 364/497, 498, 577, 578, 364/579, 580, 571

[56] References Cited

U.S. PATENT DOCUMENTS

| | | | |
|---|---|---|---|
| 4,231,097 | 10/1980 | Shibayama | 364/577 |
| 4,323,309 | 4/1982 | Akitomo et al. | 364/498 X |
| 4,368,509 | 1/1983 | Li | 364/497 X |
| 4,468,742 | 8/1984 | Jenden et al. | 364/497 |
| 4,528,565 | 7/1985 | Hauptmann | 364/577 |

Primary Examiner—Errol A. Krass
Assistant Examiner—H. R. Herndon
Attorney, Agent, or Firm—Ronald G. Cummings; Francis L. Masselle; Edwin T. Grimes

[57] ABSTRACT

A method and apparatus to optimize a characteristic of measured data in an adjustable instrument for chemical analysis. The characteristic is measured at a plurality of adjustment points about a start point. Through parabolic interpolation of the data a conjugate vector is formed and the best operating point thereon is selected. Then measurements of the characteristic are taken as a function of the adjustable parameters about the best point on the conjugate vector. These data are used in a parabolic interpolation to define a second conjugate vector. The best operating point on the second conjugate vector is the optimum point of the instrument.

20 Claims, 12 Drawing Figures 1 ppm Mn

BEFORE OPTIMIZATION: POWER 1050 WATTS
VIEWING HEIGHT 12 MM
NEB. FLOW 0.9 l/MINUTE

OPTIMIZATION RANGES:
POWER    500 – 1600
HEIGHT     8 –   30
NEB. FLOW  0.3 –  1.6

1 ppm Mn

AFTER OPTIMIZATION: POWER 710 WATTS
VIEWING HEIGHT 20MM
NEB. FLOW 0.91 l/MINUTE

ELAPSED TIME:
11 MINUTES/MONOCHROMATOR
(CURRENT FIRMWARE)

6 MINUTES/MONOCHROMATOR
(IMPROVED FIRMWARE)

20 mm
1160 WATTS
1.00 l/mm 503.1

PEAK MAXIMUM
HALF MAXIMUM
SPECTRUM MINIMUM 588.935

$W_1$ = 52.2 GRATING STEPS
$W_2$ = 15 GRATING STEPS 21 mm
960 WATTS
1.52 l/min 588.935

326.3

OPTIMIZATION APPARATUS AND PROCEDURE

FIELD OF THE INVENTION

The present invention relates to an optimization procedure for operating an instrument for chemical analysis and, in the preferred embodiment, to a procedure for optimizing the operation of an inductively coupled plasma spectrometer.

BACKGROUND OF THE INVENTION

In the field of chemical analysis, many instruments have been developed for assisting in determining the composition of samples. Such instruments are well known to research chemists who use the instruments daily in their work. The experiments performed frequently require the selection of various instrument operating parameters. In the inductively coupled plasma (ICP) spectrometer such as the Perkin-Elmer ICP-6000, for example, the power level, the height above the excitation coil where measurements are taken and the rate of flow of the nebulizer gas are all manually adjustable. The setting for each of these adjustable controls has a substantial effect on the operation of the instrument. If the setting is correct, the results are highly useful. However, if the setting is wrong, the data from an experiment may give misleading results. Therefore, in the operation of such instruments, the skill and knowledge of the operator greatly affects the validity of the results. In addition, even skilled operators may spend a substantial amount of time in determining the proper setting of the adjustable instrument operating parameters before meaningful results can be achieved.

In view of the above stated difficulties, it is the primary objective of the present invention to provide an apparatus and a method for operating that apparatus which will permit rapid and accurate determination of operating parameters of an adjustable instrument for chemical analysis.

It is a further objective of the present invention to provide an apparatus and a method for operating the apparatus which quickly and accurately determines the operating parameters which give near optimum results without requiring the intervention of an operator to interpret intermediate test results and prescribe subsequent experiments with new instrument operating parameters.

BRIEF DESCRIPTION OF THE INVENTION

The apparatus includes an instrument such as an inductively coupled plasma spectrometer with a plurality of adjustable parameters such as power level, flow rate of the nebulizer gas and height above the induction coil at which spectrometer readings are taken. The adjustable parameters can be set in response to control signals received from a microprocessor.

The microprocessor receives input from the operator in the form of the ranges for the adjustable parameters. The microprocessor then selects operating conditions at the midpoint of the range for each adjustable parameter which define a "start point." Then, an experiment is performed at these operating parameters. The resulting data are then analyzed to determine the value of a particular characteristic of the data which is to be optimized. Thereafter, each adjustable parameter is altered one at a time by +20% and then −20% of the range selected by the operator and the characteristic to be optimized is measured.

Once all these experiments have been performed, three points are defined for the characteristic to be optimized as a function of each adjustable parameter. A parabolic interpolation is performed for each of these three data point sets to calculate the value on each parabola where the characteristic to be optimized is optimum. The optimum points for each parameter comprise the coordinates of the end of a "conjugate vector" which starts at the start point and ends at a first test point. The conjugate vector is doubled and the end point defines a second test point. Measurement of the characteristic to be optimized are made at the first test point and the second test point. Then, through parabolic interpolation of the characteristic to be optimized with respect to each adjustable parameter at the start, first test and second test points, a third test point for each parameter is determined.

Thereafter, the instrument is operated at the new optimum point and the characteristic to be optimized is measured. Then, each adjustable parameter is varied by +10% and −10% of the range selected by the operator and the characteristic to be optimized is measured for each setting of the adjustable parameters. The three measurements of the characteristic to be optimized for each adjustable parameter are utilized in another parabolic interpolation and a fourth test point is identified on a second conjugate vector between the third and fourth test points. A fifth test point is located at the end point of a vector starting at the third test point, lying along the second conjugate vector, and twice as long as the second conjugate vector. The value to be optimized is calculated at the third, fourth and fifth test points. By parabolic interpolation of data, the optimum point on the vector passing through test points three and five is determined. The characteristic to be optimized is then measured at this optimum point. Tests have shown that this optimum point is close enough to the peak to yield accurate enough measurements that further iterations of the process are not required.

BRIEF DESCRIPTION OF THE DRAWINGS

The above-mentioned objects, advantages and features of the present invention are described below in greater detail in conjunction with the drawings which form a part of the original disclosure wherein.

DETAILED DESCRIPTION

Figure 1:
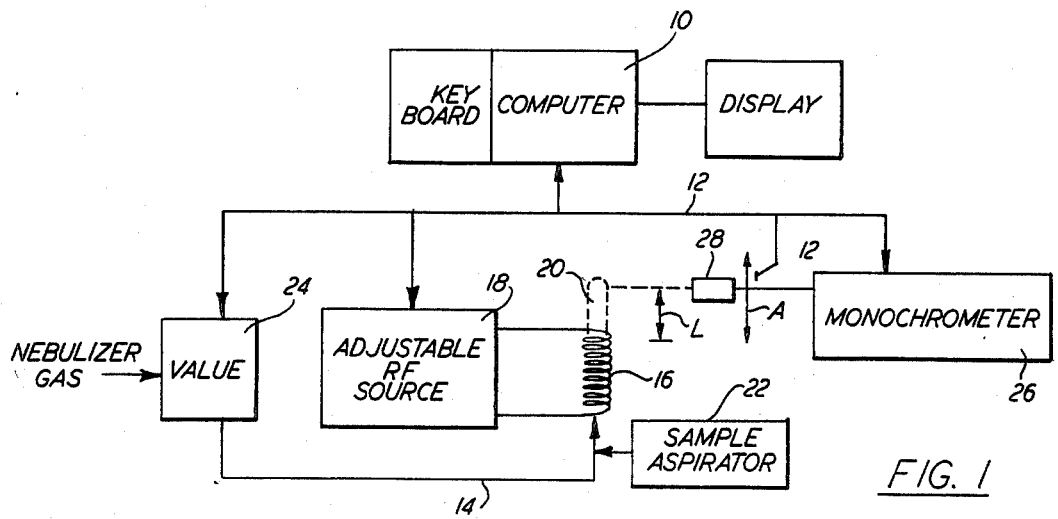
FIG. 1 is a block diagram of an ICP spectrometer which includes the optimization apparatus and utilizes the optimizing procedure of the present invention.

Referring now to FIG. 1, the apparatus of the preferred embodiment of the present invention is illustrated in block diagram form. The apparatus includes a computer 10 which sends and receives data over a communication bus 12. In the preferred embodiment, the computer 10 comprises a Perkin-Elmer Model 7500 computer although another computer could be utilized. The communication bus 12 may be any appropriate communication bus which can couple a computer 10 to one or more peripheral devices.

In the present invention in its preferred form the computer 10 communicates via the bus 12 to a plurality of peripheral devices which control adjustable parameters of the instrument. In the preferred embodiment, one such adjustable parameter is the nebulizer gas flow through the tube 14 which is directed along the axis of an induction coil 16. A sample to be tested is introduced by the sample aspirator 22 into the gas flowing through the coil 16. The rf power applied to the coil 16 by the adjustable RF source 18 is inductively coupled to the gas and the aspirated sample carried thereby causing them to be rapidly heated and issue from the top of the coil as a plasma flame 20. The plasma flame 20 is affected by the rate of nebulizer gas flow through the coil 16, the gas flow rate being controlled by the adjustable valve 24 which is controlled by signals received from the computer 10 over bus 12.

The instrument of FIG. 1 also includes a monochrometer 26 which has a detector 28 disposed near the plasma flame 20 in such an orientation that the detector 28 can be used to detect the emission from the plasma flame 20. The monochrometer 26 produces data which defines an emission curve as a function of wave length. This data is collected by the monochrometer circuitry and transmitted to the computer 10 over the bus 12.

The height L of the detector 28 above the top of the coil 16 is adjustable under control of the computer 10. By transmitting a signal to the detector positioner over line 12', the detector 28 can be caused to move up or down in the direction of the double headed arrow A relative to the plasma flame 20. This movement can easily be accomplished by mounting the detector 28 on a bracket and providing a way to move the bracket in the vertical direction such as by a rack and pinion gear powered by a stepping motor. Alternatively, adjustable optics including mirrors can be used to project the emission from a selected height in the plasma flame 20 onto the detector 28 which is fixed at a particular location.

The power level of the rf source 18 is also controllable by the computer 10. The computer sends data to the rf source 18 over the bus 12 to adjust the power applied to the coil 16.

Figure 7:
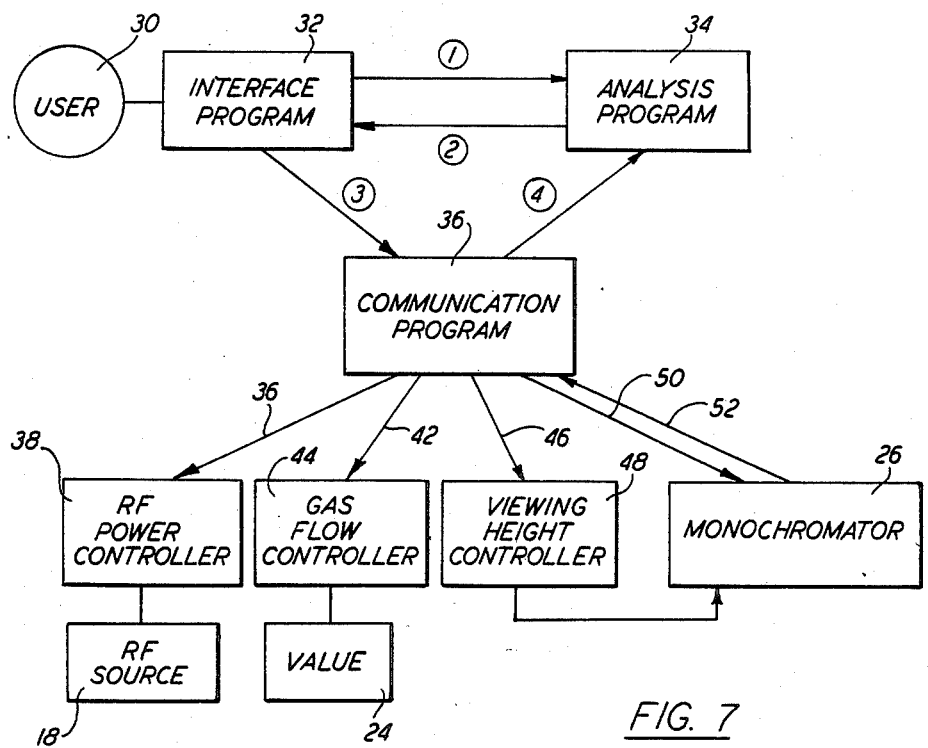
FIG. 7 illustrates the flow of control signals and data between the hardware and the software of the computer of FIG. 1.

The computer 10 and the adjustable elements of the instrument coupled thereto as illustrated in FIG. 1 are controlled by a plurality of interacting programs, the interaction of which is illustrated in FIG. 7. The user interface with the computer is illustrated at 30 and typically comprises a keyboard entry in response to an inquiry placed on the screen of the display associated with the computer. In the operation of the present invention, the user is requested to enter the ranges for the adjustable parameters of the instrument. For example, the user might be asked to specify the range of nebulizer gas flow to thereby define the upper gas flow rate and the lower gas flow rate in which the instrument is to optimize operation. The user may also be requested to specify the range of power utilized in the adjustable rf power source. In addition, the operator may be requested to specify the range of heights in the plasma flame whereat measurements are to be taken. These three specific adjustable parameters are provided by way of example and are not intended to be inclusive of all possible adjustments which might be placed under automatic control and subject to adjustment during the optimization process in accordance with the present invention. The questions placed upon the screen of the computer 10 and the data input thereto by the user through the user interface 30 is processed by an interface program 32. Once the data have been entered, the interface program 32 transmits the adjustable parameter ranges to an analysis program 34. The analysis program 34 uses these data to determine the midpoint of the ranges for each adjustable parameter so as to define the starting point for each such parameter. It should be noted that in the preferred embodiment, the analysis program 34 selects the midpoint of each adjustable parameter's range, however, some other point within that range might arbitrarily be selected.

The analysis program 34, upon determining the starting operation point for each adjustable parameter, transmits these data back to the interface program 32 which in turn transmits that information to a communications program 36 which directs the control information with respect to each adjustable parameter to the hardware for adjusting that parameter. For example, the data relating to the starting operating point for the adjustable rf source are transmitted over the line 36 to an rf power controller 38 which is coupled to the adjustable rf source 18. The controller 38 in cooperation with the rf source 18 causes a given power level of radio frequency energy to be applied to the induction coil 16. In a similar fashion, the communications program 36 transmits the starting gas flow data over the line 42 to a gas flow controller 44 which couples to the controllable valve 24. The gas flow controller 44 and the valve 24 in response to the data received on the line 42 sets the nebulizer gas flow rate to the selected value. The flowing gas is then caused to flow through the induction coil 16 at the starting operating point for this adjustable parameter.

The communication program 36 also provides data, over the line 46, specifying the viewing height in the plasma flame which is received by a viewing height controller 48 which is coupled to the monochrometer 26. The viewing height controller 48 and the monochrometer 26 in response to the starting operating point for the viewing height cause the detector 28 to be positioned relative to the flame 20 so as to intercept radiation emanating from that specified height within the flame 20.

Once the monochrometer height 26, the nebulizer gas valve 24 and the rf source 18 have been adjusted to the starting operating point, the monochrometer 26 operates in a manner to collect a plurality of plots for the characteristic to be optimized as a function of the selected operating points for the adjustable parameters. This process is initiated by a request over the line 50 to the monochrometer 26 from the communications program 26. When the data have been collected, the monochrometer 26 sends that data over the line 52 to the communications program 36 which routes the data to the analysis program 34. The analysis program analyzes the data in a manner to be described later, however, once that analysis is complete, the analysis program issues commands to the interface program which routes those commands via the communications program 36 to the rf power controller 38, gas flow controller 44 and the viewing height controller 48 so as to adjust these adjustable parameters to a new value in accordance with the procedures set forth below in conjunction with FIGS. 2-6. Accordingly, a plurality of tests are conducted each of which produces data that are transmitted via the communications program 36 to the analysis program 34 which analyzes the data and produces information defining further alternate tests.

Figure 2:
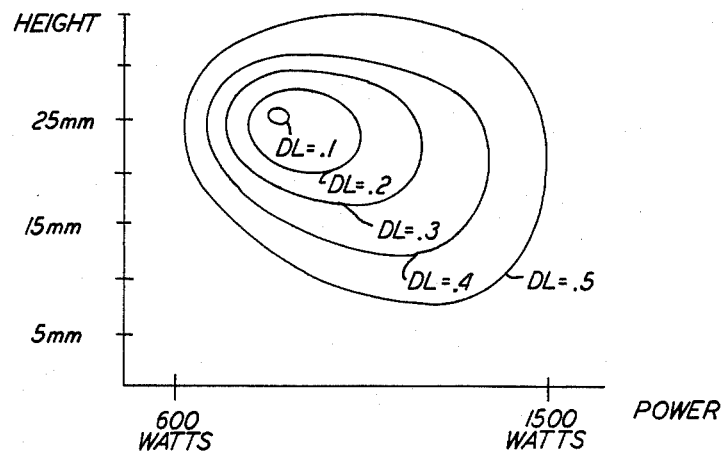
FIG. 2 shows the contours of constant detection limit as a function of detection height and power level.

Referring now to FIG. 2, a plurality of generally ovally shaped plots of the detection limit as a function of the height and the rf power is shown. The abscissa and the ordinate of FIG. 2 can be changed, if it is desired, so as to provide a plot of detection limit, as a function of other adjustable parameters. It will also be recognized by those of skill in the art that a third dimension could be drawn to the figure so that the plot of the detection limit can be represented as a function of three adjustable parameters. If this were to be done in FIG. 2, the third axis would be drawn perpendicular to the page and the plot of the detection limit would then comprise surfaces as opposed to lines as illustrated in FIG. 2. For simplicity, however, the operation of the present invention will be described in most detail where only two adjustable parameters are varied and all other adjustable parameters are maintained at a constant value. In operation, however, the instrument according to the present invention varies all of the adjustable parameters but the procedure for optimization is essentially as will be described below.

Figure 3:
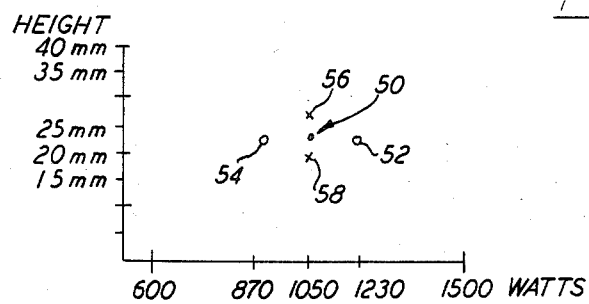
FIG. 3 illustrates the test points for the first part of the optimization procedure.

It shall be assumed that the operator has specified to the instrument through the user interface 30 of FIG. 7 that the power range for the adjustable rf source is between 600 and 1500 watts and that the height in millimeters above the top of the induction coil ranges between 20 and 30 millimeters. Accordingly, as illustrated in FIG. 3, the starting point for the optimization procedure is shown at 50 and corresponds to an operating point where the adjustable rf source is set to 1050 watts and the height above the coil is set to 25 millimeters. This starting point corresponds to a point lying midway between the extremes of each range for an adjustable parameter of the instrument. As has already been mentioned, selection of the midpoint is an arbitrary selection and it is possible to select other starting points if it is desired to do so.

At the starting point 50, the analysis program 34 of FIG. 7 causes the monochrometer 26 to produce a plurality of measurements of the characteristic which is to be optimized. For the illustrated example, the characteristic to be optimized is the detection limit which is defined to be the concentration of the element whose spectrum shows a peak which is twice the standard deviation of the baseline. In order to optimize the detection limit, the instrument must be adjusted such that the detection limit for the selected adjustments of the adjustable parameters is as small as possible.

In accomplishing this as illustrated in FIG. 3, the instrument is operated at the starting point 50 where the power and the height are at the midpoint of the operating range as specified by the user. When operating at that point, the instrument measures the detection limit at the starting point. Then, the power level is adjusted away from the starting point while the other adjustable parameters remain the same. For the preferred embodiment of the present invention, the power level is adjusted so that it is 20% of the operator selected range above the starting point as indicated by the circle 52 (at 1230 watts) and the detection limit is measured under these operating conditions. Then, the power level is adjusted so that it is 20% of the operator selected range below the starting point as indicated by the circle 54 (at 870 watts) and the detection limit is measured thereat. Thereafter, the power level is returned to that at the starting point and the height is varied to a point 20% of the range for the height above the starting point (at 27 mm) as indicated at the X 56. The detection limit is measured under these conditions. Thereafter, the height is adjusted to be 20% of the range for the height below the starting point (at 23 mm) as indicated at the X 58. The detection limit is measured at this point as well.

After these measurements are conducted and in the event that the gas flow rate is also adjustable, the gas flow is adjusted to a point which is 20% of the range of gas flow above the starting point and the detection limit is measured thereat. Thereafter, the gas flow is adjusted to a point 20% of the range below the starting point and the detection limit is measured thereat.

Figure 4A:
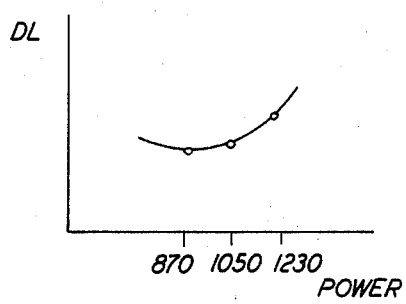
FIGS. 4A and 4B illustrate typical curves obtained from parabolic interpolation of the data calculated at the test points illustrated in FIG. 3.
Figure 4B:
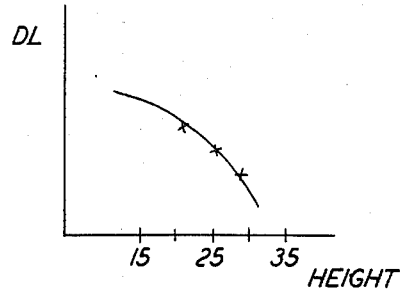
Figure 5:
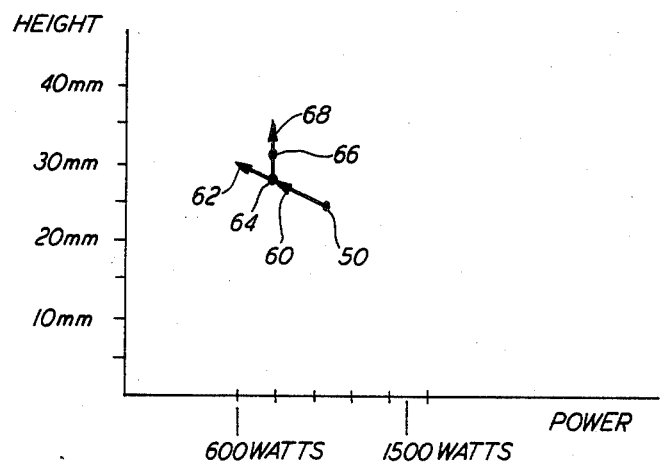
FIG. 5 illustrates the "conjugate vector" determined by the optimum points determined from the curves of FIGS. 4A and 4B.

With three measurements of the detection limit as a function of each independently adjustable parameter being complete, it is possible to define curves such as illustrated in FIGS. 4A and 4B which plot the detection limit versus each adjustable parameter. Then, through the well known process of parabolic interpolation, a parabola passing through the three measurement points is constructed such as is illustrated in FIGS. 4A and 4B. Then, the minimum point on that parabola within the range of the adjustable variable is determined and this lowest operating point on each parabola comprises one of the operating coordinates of a first test point 60 as illustrated in FIG. 5. The starting point 50 and the first test point 60 comprise the end points of a vector known as the conjugate vector. With the direction and length of the conjugate vector being known as the coordinates of the starting point 50 and the coordinates of the test point 60 are known, it is possible to double this vector to define a second test point 62 at the end of this double conjugate vector. For the time being it will be assumed that the values of the adjustable parameters at the second test point all lie within the specified range. Then, the detection limit is measured at the first test point 60 and the second test point 62. From the parabolic interpolation of these data, an additional parabola is produced as in FIG. 6 and the minimum thereof within the operating range of the adjustable parameter is then selected. This selection process is equivalent to selecting the most optimum operating point lying along the vector starting at the starting point 50 and ending at the second test point 62. This point comprises a third test point which is illustrated at 64 in FIG. 5.

The procedure as illustrated with respect to the starting point 50 in FIG. 3 is then repeated with respect to the third test point 64 in FIG. 5, however, the range of deviation of each of the adjustable parameters is smaller than that initially taken with respect to the starting point 50. In the preferred embodiment, the deviation of each adjustable parameter from that at the third test point 64 is selected to be either plus or minus 10% of the range for each adjustable parameter. Hence, the power level can be adjusted by plus or minus 90 watts and the height can be adjusted by plus or minus 1 millimeter for the example being illustrated as the initial range for the power is 900 watts and for the height 10 millimeters.

More specifically, at point 64 the detection limit is measured. Then, the power is adjusted upward by 90 watts and the detection limit is measured. Thereafter, the power is set to 90 watts below that at point 64. Once the power is returned to that at point 64, the height is raised by 1 mm and the detection limit measured. Then the height is lowered by 1 mm and the detection limit measured again. By parabolic interpolation of the data, a fourth test point 66 is defined which lies at the end of a second conjugate vector starting at point 64 and ending at point 66.

Figure 6:
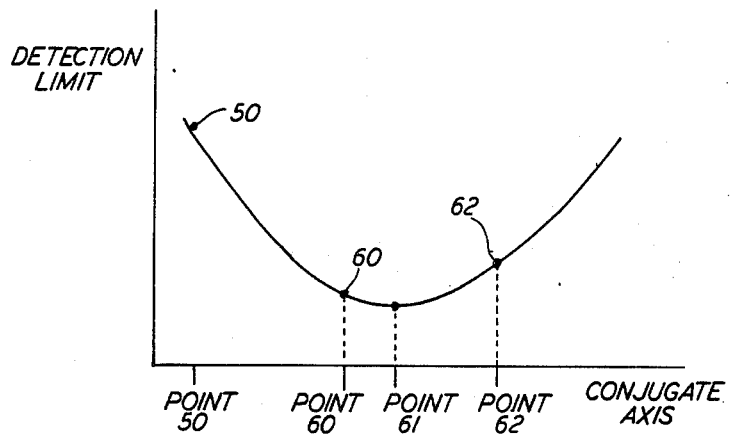
FIG. 6 illustrates the parabolic interpolation of the data when the characteristic to be optimized is measured at the start point, the optimum point and the alternate test point.

The second conjugate vector is then doubled and the end point thereof is a fifth test point 68. With measurements of the detection limit at the third, fourth and fifth test point, a parabola such as that in FIG. 6 is defined. The minimum point on that curve is the final optimum test point. Measurement of the characteristic to be optimized is then made at the final optimum test point. Testing has shown this point is close enough to the absolute optimum point that further testing from a practical sense is not required.

The above description has placed particular emphasis upon an apparatus designed for maximizing the detection limit in an inductively coupled plasma spectrometer. The emphasis has been particularly on an instrument of that type wherein the power level of the rf source is adjustable as well as is the height at which the system monochrometer monitors the emission from the flame. As is evident from the above description, however, it is possible to vary other operating parameters of the instrument and these variable parameters do have an effect on the ability of the instrument to measure, for example, the detection limit. One such adjustable parameter is the nebulizer gas flow which, as illustrated in FIG. 1, passes through a controllable valve 24 and a conduit 14 and eventually into the induction coil 16. Prior to the entry of the gas into the induction coil 16, however, a sample aspirator 22 injects a small amount of the sample into the nebulizer gas. In the preferred embodiment, the nebulizer gas is argon and it has been shown that the nebulizer gas flow rate into the induction coil does have a significant effect on the detection limit.

Figure 8A:
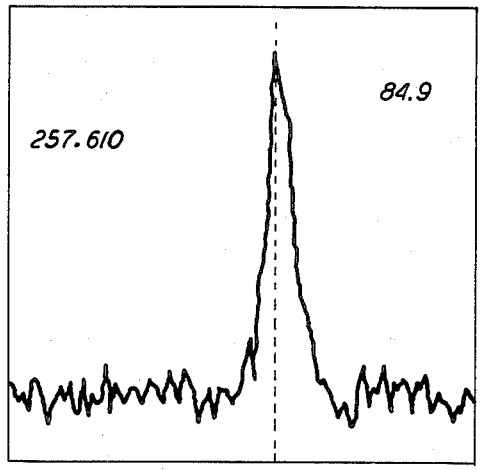
FIGS. 8A and 8B illustrate typical optimization of the detection limit using the apparatus and procedure of the present invention.
Figure 8B:
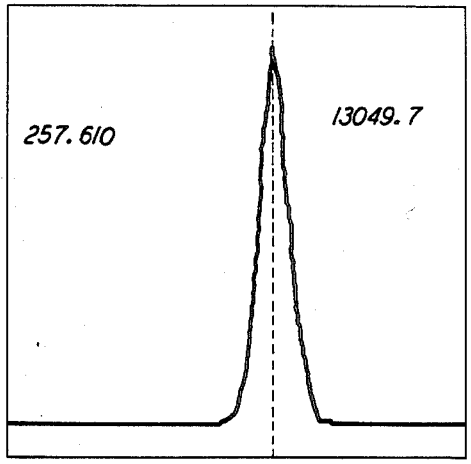

In operation, the instrument as illustrated in FIG. 1 yields optimization as illustrated in FIGS. 8A and 8B. Specifically, a sample containing one part per million of manganese was introduced into the nebulizer gas and the instrument was adjusted so that the rf power source provided 1050 watts, the viewing height was 12 millimeters and the nebulizer gas flow rate was 0.9 liters per minute. Under these conditions, an emission intensity of 84.9 was measured at the wavelength of 257.610 nanometers, the characteristic frequency for emission of manganese. This is illustrated in FIG. 8A. The most important aspect of FIG. 8A, however, is that the base line is very noisy and comprises a significant percentage of the height of the emission intensity peak at the wavelength of interest.

The optimization, in accordance with the present invention, was then conducted and the operator specified that the power range should be between 500 and 1600 watts, the height between 8 and 30 millimeters and the nebulizer flow between 0.3 and 1.6 liters per minute.

In approximately six minutes, the optimizer was able to determine an optimum point of operation. At this optimum point, the power was 710 watts, the viewing height 20 millimeters and the nebulizer flow rate was 0.91 liters per minute. Under these conditions, a plot of the emission intensity versus wavelength was produced as illustrated in FIG. 8B. In this particular case, the emission intensity for a sample containing one part per million manganese was 13,049.7 at the wavelength of 257.610 nanometers. The important feature of this optimization, however, is the fact that the base line as illustrated in FIG. 8B is essentially flat in comparison to the peak. Accordingly, one must conclude that the optimization procedure as illustrated above for the example illustrated in FIG. 8A and FIG. 8B has indeed selected an instrument operating point which is far superior to the operation point selected prior to optimization. Additionally, the time required to perform this optimization is very small compared to the time that might be required for an operator to manually adjust the instrument and perform a plurality of experiments in the hope of finding an operating point which would give better results than were achieved at the operating conditions which gave rise to the plot of FIG. 8A.

Figure 9A:
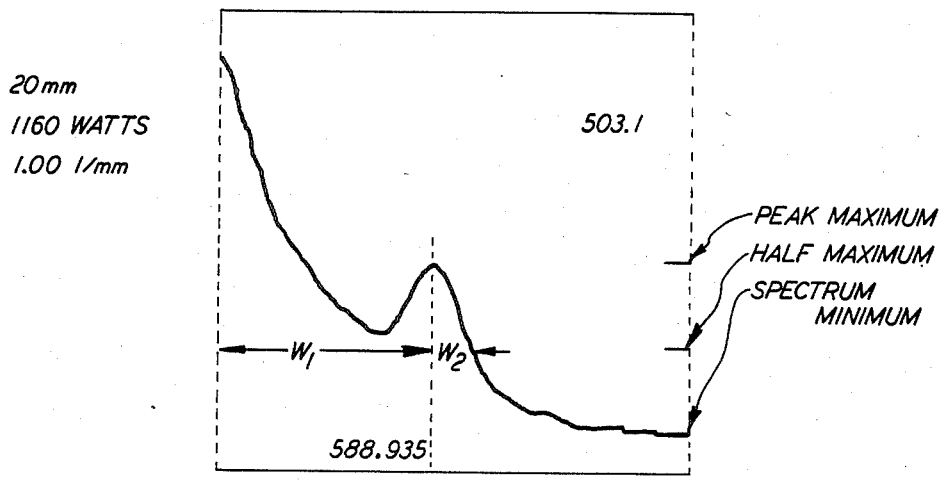
FIGS. 9A and 9B illustrate typical optimization of specral interference using the apparatus and procedure of the present invention.

A further characteristic which can be optimized in accordance with the present invention is that of spectral interference. Spectral interference is illustrated in FIG. 9A where, for example, the peak at 588.935 nm is interfered with by the peak at a lower wavelength for argon, the typical nebulizer gas used in the present invention. In the plot in FIG. 9A, the sodium peak at wavelength 588.935 nm is 503.1, however, the peak is not well defined as can be seen to the left of the peak where the detector output is actually higher than at the peak which represents the presence of sodium. Accordingly, the presence of argon in large quantities is interfering with the displaying of the peak associated with the presence of sodium in the sample.

In accordance with the present invention, spectral interference is minimized. Spectral interference is measured by the wider of the two half-widths at half maximum peak height. In FIG. 9A, $W_1$ is the wider of the two half-widths at half peak height. $W_1$ is measured at a height above the base line which is half that of the peak above the baseline. The narrower of the two half-widths at half peak height is with $W_2$.

In accordance with the present invention, if the spectral interference is to be optimized, an initial operating condition is selected such as those set forth in association with FIG. 9A where the emission is measured at 20 millimeters above the induction coil, 1160 watts of power is put into the induction coil and the nebulizer flow rate is one liter per minute. Then, the spectral interference as measured by the wider of $W_1$ or $W_2$ is calculated and the parabolic interpolation conducted in the same manner as set forth above with respect to the detection limit. The optimum point on each parabola is that which minimizes the wider of $W_1$ or $W_2$. After 4N plus 7 experiments have been conducted, where N is the number of adjustable parameters for the instrument, the last experiment is deemed to be at an operating condition which is sufficiently close to the optimum that further use of the present optimization procedure is unnecessary.

Figure 9B:
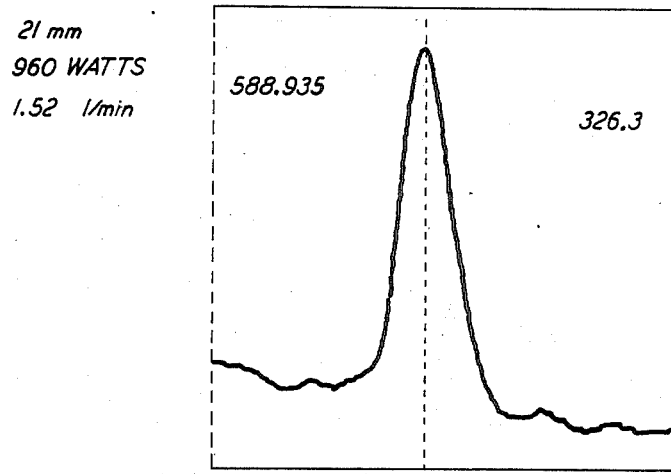

In the case of the present invention, the optimum setting for the adjustable parameters is illustrated in FIG. 9B where the height above the coil is 21 millimeters, the power into the coil is 960 watts and the nebulizer flow rate is 1.52 liters per minute. Under these conditions, the sodium peak at a wavelength of 588.935 nm is 328.3. While it should be noted that this peak is lower than the peak maximum as illustrated in FIG. 9A, the peak of FIG. 9B is much better defined and, accordingly, is better suited for further analysis than is the larger though less defined peak of FIG. 9A.

In addition to optimizing the detection limit and spectral interference, the technique according to the present invention is equally applicable to optimizing further characteristics of measurements made by the instrument according to the present invention. Specifically, peak precision can be optimized. Peak precision is a measurement of the standard deviation of a given peak divided by the height of that peak. In addition, the instrument according to the present invention can be utilized to optimize the signal to background ratio. This ratio is determined by measuring the height of a peak above the background noise divided by the background.

The present invention is also useful in optimizing any of the above-mentioned characteristics by adjusting additional adjustable parameters of the instrument. As has already been pointed out, the height above the induction coil, the power into the induction coil and the nebulizer flow gas rate can be adjusted and these adjustments have an effect on the characteristic to be optimized for a sample. In addition to adjusting the above-mentioned parameters, the present invention is also useful in optimizing characteristics of the measurement by adjusting the plasma gas flow, the auxiliary gas flow, the sample injection rate as well as the voltage on the photo multiplier tube used within the monochrometer.

The software illustrative of the type needed to achieve the optimization and perform the method steps as set forth above is set forth below in the appendix pages 1-13. This software listing is in the C-language and may be compiled on a Perkin-Elmer 7500 and will operate in the manner herein described above. Other programs can easily be developed in other programming languages to accomplish the same functions.

It has been noted above that the adjustments made to the adjustable parameters were assumed to be within the operating range of that particular parameter as selected by the operator. By necessity, the first set of experiments conducted about the starting point are within that range. However, once the first conjugate vector is formed, it is possible that the coordinates of the end of twice that conjugate vector can lie outside of the operating range selected by the operator. When this occurs, the conjugate vecor must be modified so that all the adjustable parameters at the end point of the double conjugate vector lie within the selected operating range. This is done by setting the value of the adjustable parameter which goes out of range to one that lies within range and the other adjustable parameters are scaled proportionally. Accordingly, the coordinate of the end point of twice the conjugate vector for that one adjustable parameter is at the limit of the range. At the first test point, that adjustable parameter is one half the difference between the value of the adjustable parameter at the end of the double conjugate vector and at the starting point. It will also be recognized that this same adjustment to the double conjugate vector which starts at the starting point may be necessary for the point defining the end of the second conjugate vector formed in the process according to the present invention.

It should also be noted that the +10% or −10% excursion about point 64 must be within the range for each adjustable parameter. Accordingly, the adjustment is either 10% of the range or to the limit for that parameter, whichever is smaller.

While parabolic interpolation has been illustrated and is utilized in the preferred embodiment of the present invention, other interpolation methods can be utilized. The element of each interpolation method which is deemed important is that the curve produced by the interpolation have a non-zero second derivative, such other interpolation methods can be utilized in place of parabolic interpolation if it is desired. Parabolic interpolation has the advantage, however, of being relatively easy to implement and only three points need be measured to produce a parabola. This means the number of experiments needed to arrive at the optimum condition for the adjustable parameters is low compared to most other approaches.

The foregoing discussion has been made with particular emphasis upon a preferred embodiment therefor which utilizes a particular form of instrument for chemical analysis namely, the inductively coupled plasma spectrometer. Those of skill in the art, however, will recognize that the principles of the present invention may be applied equally to the operation of various other instruments for chemical analysis. Furthermore, the particular computer which is utlized in conjunction with the operation of the instrument is preferably a Perkin-Elmer Model 7500 although a Perkin-Elmer Model 7300 and other similar computers may be utilized as well. The foregoing and other modifications to the apparatus according to the present invention may be made by those of skill in the art without departing from the spirit and scope of the present invention as defined by the following claims.

APPENDIX

```
#include <std.h>
#define BUFSIZE 128
#define NUM_PARM 3    /* number of instrument settings to optimize */
#define NUM_COND 5    /* number of decision criteria */
#define NUM_READS 50  /* number of readings for precision measurements */
#define NUM_RDS_TM 50 /* number of reads for Tracy-Myers correlations*/
#define NCYCLES 2     /* number of Fletcher - Powell cycles to do */
#define TOOSMALL 1.0e-10    /* a small number */
IMPORT FLOAT max_x();    /* get fractional step number */
IMPORT FLOAT eval_func();
IMPORT FLOAT parabola(), parm_scale();
IMPORT DOUBLE sqrt();
IMPORT FLOAT find_width();    /* returns FWHM in steps */
IMPORT COUNT find_min();
IMPORT COUNT max_pos();    /* returns position of max. intens. */
```

```
IMPORT UTINY parm_check();   /* checks parameters for invariance */
IMPORT FLOAT nm_per_step();  /* stepsizeas a func. of grating, wavelength */
IMPORT DOUBLE phase();       /*compute the phase relation between A and R data*/

/* optimize - find optimum instrument conditions
 */
VOID optimize(databuf, ndata, range, weights, mc, uci, lci, wl, bgcflag)
    FLOAT databuf[][3][BUFSIZE - 1];
    COUNT ndata;
    FLOAT range[][NUM_PARM][2];
    FLOAT weights[][NUM_COND];
    UTINY mc;
    TEXT uci[][5], lci[][5];
    TEXT wl[][8];
    UTINY bgcflag[];    /* background correction flag */

{
    GLOBAL TEXT hdr[2][3][4];    /* data header from the monochromator */
    LOCAL TBOOL start_flag[2] = (NO);   /* is optimization in progress ? */
    LOCAL TBOOL conj_vector[2] = (NO);  /* is this a conjugate direction */
    LOCAL UTINY curr_parm[2] = (0); /* current parameter being explored */
    FAST COUNT i;
    LOCAL FLOAT opt_parm[2][NUM_PARM];   /* estimated optimated values */
    LOCAL FLOAT parm[2][NUM_PARM];       /* current values of parameters */
    LOCAL FLOAT save_parm[2][NUM_PARM];  /* save a set of parameters */
    LOCAL FLOAT t_parm[2][3];      /* temporary values of a single paramater */
    LOCAL FLOAT func_value[2][3];      /* three values of optimization function */
    LOCAL FLOAT eval_cond[2][NUM_COND]; /* evaluation measurements */
    LOCAL FLOAT delta[2][NUM_PARM]; /* changes in paramters used for conjugate vector */
    LOCAL FLOAT v_scale[2]; /* used to scale opt_parm s.t. conjugate vector stays in bounds */
    /* opt_est not used */
    FLOAT opt_est;  /* optimum point on conjugate vector */
    LOCAL FLOAT old_opt[2] = (0.0, 0.0);
    LOCAL FLOAT new_opt[2] = (0.0, 0.0);
    LOCAL FLOAT radius[2] = (0.2, 0.2); /* fraction of range in which to search */
    LOCAL FLOAT wave_l[2];  /* wavelengths */
    LOCAL DOUBLE sumx[2]  = (0.0, 0.0);
    LOCAL DOUBLE sumx2[2] = (0.0, 0.0);
    LOCAL DOUBLE sumy[2]  = (0.0, 0.0);
    LOCAL DOUBLE sumy2[2] = (0.0, 0.0);
    LOCAL DOUBLE sumxy[2] = (0.0, 0.0);
    LOCAL COUNT rep_count[2] = (0, 0);
    LOCAL UTINY cycle_count[2] = (0, 0);
    LOCAL TBOOL prec_done[2] = (NO, NO);
    LOCAL TBOOL dl_dcne[2] = (NO, NO);
    LOCAL cycle_done[2] = (NO, NO);
    COUNT imax;
    LOCAL UTINY curr_step[2] = (0, 0);
    LOCAL FLOAT peak_mean[2] = (0.0, 0.0);
    LOCAL FLOAT peak_stddev[2] = (0.0, 0.0);
    LOCAL FLOAT wl_save[2];      /* save nominal wavelength */
    LOCAL FLOAT vec_length[2];   /* opt. point on conjugate search vector*/
    FLOAT mean, stddev;      /* to pass to 'stats' */
    LOCAL TBOOL init_flag[2] = (NO, NO);
    LOCAL TBOOL wl_flag[2] = (NO, NO);   /* record if wl has been received */
    TEXT mcid = (mc == 0) ? 'A' : 'B';
    LOCAL COUNT lindex[2] = (0);
    LOCAL COUNT rindex[2] = (0);
    LOCAL COUNT n_save[2] = (0);    /* to remember spectrum size */
    LOCAL COUNT num_reads[2] = (NUM_READS);
    LOCAL COUNT num_save[2] = (NUM_READS);   /* use for Tracy-Myers opt.'s*/
    COUNT index;
    GLOBAL COUNT peak[2];    /* search window in steps */ if (start_flag[mc] && !wl_flag[mc])
        {
        encode(&wl[mc][0], 7, "%f", &wave_l[mc]);
        wl_save[mc] = wave_l[mc];   /* save nominal wl */
        wl_flag[mc] = YES;
        }
    if (ndata <= 0) /* reset flags (HZ0 received by q9read) */
        {
        cycle_done[0] = cycle_done[1] = NO;
        conj_vector[0] = conj_vector[1] = NO;
        old_opt[0] = old_opt[1] = 0.0;
        new_opt[0] = new_opt[1] = 0.0;
```

```
            radius[0] = radius[1] = 0.2;
            sumx[0] = sumx[1] = 0.0;
            sumx2[0] = sumx2[1] = 0.0;
            curr_parm[0] = curr_parm[1] = 0;
            curr_step[0] = curr_step[1] = 0;
            rep_count[0] = rep_count[1] = 0;
            cycle_count[0] = cycle_count[1] = 0;
            prec_done[0] = prec_done[1] = 0;
            dl_done[0] = dl_done[1] = 0;
            init_flag[mc] = start_flag[mc] = NO;     /* reset only one flag!!!!!!! */
            wl_flag[0] = wl_flag[1] = NO;
            if (ndata < 0)   /* optimization completed */
                return;
            }
    if (!start_flag[mc])   /* initialize */
        {
        for (i = 0; i < NUM_PARM; ++i)  /* initialize to centroid */
            if (range[mc][i][1] >= 0.0)
                parm[mc][i] = (range[mc][i][1] + range[mc][i][0])/2.0;
            else
                parm[mc][i] = range[mc][i][0];
        norm_parm(&parm[mc][0]);    /* normalize parameters to rounded values */
        for (i = 0; i < NUM_PARM; ++i)
            opt_parm[mc][i] = save_parm[mc][i] = parm[mc][i];
        init_flag[mc] = start_flag[mc] = YES;
        wave_l[mc] = 0.0;   /* initialization condition */
        /* ask for spectrum */
        talk_to_p2(&parm[mc][0], (UTINY)0, &wave_l[mc], mc, &new_opt[mc]);
        curr_step[mc] = curr_parm[mc] = 0;
        /* vary the first variant parameter */
        curr_parm[mc] = parm_check(range, mc, curr_parm[mc]);
        cycle_done[mc] = NO;
        /* with new RINT command, always do 50 RINT's */
        if ((weights[mc][1] < TOOSMALL) && (weights[mc][2] < TOOSMALL)
            && (weights[mc][4] < TOOSMALL))
            num_reads[mc] = 50;
        else
            num_reads[mc] = NUM_READS;
        if (weights[mc][4] > TOOSMALL)   /* T-M opt. */
            num_reads[mc] = NUM_RDS_TM;
        num_save[mc] = num_reads[mc];    /* used if Tracy-Myers opt */
        return;
        }
    if (hdr[mc][0][3] > 127)     /* read intensity or spectrum ? */
        for (i = 0; i < ndata; ++i)
            { /* read intensity block - B */
            sumx[mc] += databuf[mc][0][i];
            sumx2[mc] += databuf[mc][0][i] * databuf[mc][0][i];
            if (weights[mc][4] > TOOSMALL)   /* T-M opt. */
                {
                sumy[mc] += databuf[mc][2][i];   /* reference channel */
                sumy2[mc] += databuf[mc][2][i] * databuf[mc][2][i];
                sumxy[mc] += databuf[mc][0][i] * databuf[mc][2][i];
                }
            rep_count[mc]++;
            }
    else
        { /* read spectrum block - A */
        o_txt1(parm ,mc);    /* write out instrument settings */
        num_reads[mc] = num_save[mc];   /* restore RINT count */
        index = (ndata - peak[mc]) >> 1;    /* search only in peak window */
        imax = index + max_pos(&databuf[mc][0][index], peak[mc]);
        eval_cond[mc][0] = find_width(&databuf[mc][0][0], ndata, imax);
        rep_count[mc] = 0;   /* init. counter for precision reps. */
        encode(&wl[mc][0], 7, "%f", &wave_l[mc]);
        /* move to maximum intensity */
        wave_l[mc] += (imax - (ndata >> 1)) * nm_per_step(mcid, &wl[mc][0]);
        n_save[mc] = ndata; /* remember the spectrum size */
        if (bgcflag[mc])     /* compute background indices */
            {
            backgrourd(&databuf[mc][0][0], ndata, bgcflag[mc], &uci[mc][0],
                &lci[mc][0], (FLOAT)imax, nm_per_step(mcid, &wl[mc][0]),
                &lindex[mc], &rindex[mc]);
            lindex[mc] = (databuf[mc][0][lindex[mc]] < databuf[mc][0][rindex[mc]]) ?
                lindex[mc] : rindex[mc];
            }
        else    /* no bgc, use the minimum */
```

```
        {
        rindex[mc] = find_min(&databuf[mc][0][0], ndata);
        lindex[mc] = rindex[mc];
        }
    prec_done[mc] = dl_done[mc] = NO;    /* reset flags */
    talk_to_p2(&parm[mc][0], (UTINY)1, &wave_l[mc], mc, &new_opt[mc]);    /* s
lew, r_int */
    return;
    }
if (rep_count[mc] >= num_reads[mc]) /* done with repititions ? */
    { /* reps done. block B1 */
    if ((weights[mc][4] > TOOSMALL) && !prec_done[mc]) /* T-M opt. */
        eval_conc[mc][4] = 1.0/phase(sumx[mc], sumy[mc], sumx2[mc],
            sumy2[mc], sumxy[mc]);
    stats(sumx[mc], sumx2[mc], rep_count[mc], &mean, &stddev);
    sumx[mc] = sumx2[mc] = 0.0;  /* reset to zero */
    sumy[mc] = sumy2[mc] = sumxy[mc] = 0.0;  /* reset */
    if (!(prec_done[mc] || dl_done[mc])) /* peak precision */
        { /* block B1.a */
        peak_stddev[mc] = stddev;
        peak_mean[mc] = mean;
        prec_done[mc] = YES;
        /* move to background correction point */
        wave_l[mc] = wl_save[mc] + (lindex[mc] - (n_save[mc] >> 1)) *
                nm_per_step(mcid, &wl[mc][0]);
        talk_to_p2(&parm[mc][0], (UTINY)1, &wave_l[mc], mc, &new_opt[mc]);
        rep_count[mc] = 0;
        /* if T-M optimization is selected but not detection limit
        or peak precision, only one RINT is needed for the d.l.
        code block (just to fall through the code ) */
        if ((weights[mc][4] > TOOSMALL) && (weights[mc][1] < TOOSMALL)
            && (weights[mc][2] < TOOSMALL))
            num_reads[mc] = 1;
        return;
        }
    else   /* detection limit */
        { /* block B1.b */
        eval_cond[mc][1] = peak_stddev[mc] / abs(peak_mean[mc] - mean);
        eval_cond[mc][2] = 2.0 * stddev / abs(peak_mean[mc] - mean);
        eval_cond[mc][3] = mean/(peak_mean[mc] - mean); /* bg to s */
        eval_cond[mc][4] *= eval_cond[mc][1];
        dl_done[mc] = YES;  /* one point is now complete */
        func_value[mc][curr_step[mc]] = eval_func(&eval_cond[mc][0], &weight
s[mc][0]);
        /* write out readings */
        o_txt2(mc, eval_cond, peak_mean, peak_stddev, mean, stddev, func_val
ue[mc][curr_step[mc]]);
        if (parm_check(range, mc, curr_parm[mc]) >= NUM_PARM)
            {  /* no parameters to be varied */
            talk_to_p2(&parm[mc][0], (UTINY)2, &wl_save[mc], mc, &func_value
[mc][curr_step[mc]]);
            return;
            }
        if (init_flag[mc])
            {
            old_opt[mc] = func_value[mc][curr_step[mc]];
            init_flag[mc] = NO;
            }
        if (!conj_vector[mc])
            t_parm[mc][curr_step[mc]] = parm[mc][curr_parm[mc]];
        curr_step[mc]++;    /* do next step on this axis */
        if (curr_step[mc] > 2 || cycle_done[mc])
            { /* done with this axis  Block B1.b.ii */
            curr_step[mc] = 1;  /* reset step counter */
            wave_l[mc] = wl_save[mc];   /* restore nominal wavelength */
            /* store optimum position */
            if (conj_vector[mc])
                parabola(&t_parm[mc][0], &func_value[mc][0], &vec_length[mc]
);
            else
                parabola(&t_parm[mc][0], &func_value[mc][0], &opt_parm[mc][c
urr_parm[mc]]);
            if (cycle_done[mc]) /* Fletcher-Powell cycle completed ? */
                {   /* Block B1.b.j */
                ++cycle_count[mc];
                new_opt[mc] = eval_func(&eval_cond[mc][0], &weights[mc][0]);
                if (new_opt[mc] > old_opt[mc])
                    {   /* diverging. stop */
                    talk_to_p2(&save_parm[mc][0], (UTINY)2, &wl_save[mc], mc
```

```
, &new_opt[mc]);
                                return;
                                )
                        curr_step[mc] = curr_parm[mc] = 0;
                        conj_vector[mc] = cycle_done[mc] = NO;
                        for (i = 0; i < NUM_PARM; ++i) /* save new parm's */
                            save_parm[mc][i] = parm[mc][i];
                        if (cycle_count[mc] >= NCYCLES)
                            (   /* enough cycles. stop */
                            talk_to_p2(&parm[mc][0], (UTINY)2, &wl_save[mc], mc, &ne
w_opt[mc]);
                            return;
                            )
                        else
                            (
                            /* not done. initialize and do another cycle */
                            func_value[mc][0] = old_opt[mc] = new_opt[mc];
                            wave_l[mc] = wl_save[mc];   /* restore wl */
                            curr_step[mc] = 1;
                            t_parm[mc][0] = parm[mc][0];
                            parm[mc][0] += radius[mc] * (range[mc][0][1] - range[mc]
[0][0]);
                            norm_parm(&parm[mc][0]);
                            t_parm[mc][1] = parm[mc][0];
                            talk_to_p2(&parm[mc][0], (UTINY)0, &wave_l[mc], mc, &new
_opt[mc]);
                            return;
                            )
                        )
                else
                    (
                    if (conj_vector[mc])
                        (   /* move along conjugate vector */
                        for (i = 0; i < NUM_PARM; ++i)
                            (
                            parm[mc][i] = save_parm[mc][i] + 1.0 * v_scale[mc]
                                * (opt_parm[mc][i] - save_parm[mc][i]);
                            )
                        rorm_parm(&parm[mc][0]);
                        wave_l[mc] = wl_save[mc];   /* restore nominal wl */
                        talk_to_p2(&parm[mc][0], (UTINY)0, &wave_l[mc], mc, &new_opt
[mc]);
                        return;
                        )
                    else
                        ( /* continue on this axis Block B1.b.1j */
                        for (i = 0; i < NUM_PARM; ++i)
                            parm[mc][i] = save_parm[mc][i];
                        /* set new parameters */
                        if (curr_step[mc] == 1) /* add increment */
                            parm[mc][curr_parm[mc]] += radius[mc] * (range[mc][curr_
parm[mc]][1] - range[mc][curr_parm[mc]][0]);
                        if (curr_step[mc] == 2) /* subtract increment */
                            parm[mc][curr_parm[mc]] -= radius[mc] * (range[mc][curr_
parm[mc]][1] - range[mc][curr_parm[mc]][0]);
                        wave_l[mc] = wl_save[mc];
                        norm_parm(&parm[mc][0]);
                        talk_to_p2(&parm[mc][0], (UTINY)0, &wave_l[mc], mc, &new_opt
[mc]);
                        return;
                        )
                if (conj_vector[mc])    /* is this conjugate space ? */
                    ( /* Block B1.b.iii */
                    /* set to optimum point on conjugate vector */
                    vec_length[mc] = max(0.0, vec_length[mc]);
                    vec_length[mc] = min(1.0, vec_length[mc]);
                    for (i = 0; i < NUM_PARM; ++i)
                        parm[mc][i] = save_parm[mc][i] + vec_length[mc] * v_scale[mc
]
                            * (opt_parm[mc][i] - save_parm[mc][i]);
                    cycle_done[mc] = YES;
                    radius[mc] /= 2.0;  /* reduce search radius in next cycle */
                    curr_step[mc] = 0;
                    norm_parm(&parm[mc][0]);
                    talk_to_p2(&parm[mc][0], (UTINY)0, &wave_l[mc], mc, &new_opt[mc]
);
                    return;
```

```
            }
      else      /* axial space. Block B1.b.iij */
          {
          /* check for invariant parameter */
          curr_parm[mc] = parm_check(range, mc, ++curr_parm[mc]);
          if (curr_parm[mc] >= NUM_PARM) /* out of parameters */
              { /* Block B1.b.iiii */
              curr_parm[mc] = 0;  /* reset parameter counter */
              /* set conjugate vector */
              v_scale[mc] = parm_scale(opt_parm, save_parm, range, mc);
              /* scale changes s.t. conjugate vector is inbounds */
              for (i = 0; i < NUM_PARM; ++i)
                  {
                  parm[mc][i] = save_parm[mc][i] + 0.5 * v_scale[mc]
                        * (opt_parm[mc][i] - save_parm[mc][i]);
                  }
              rorm_parm(&parm[mc][0]);
              conj_vector[mc] = YES;
              wave_l[mc] = wl_save[mc];   /* restore wavelengh */
              talk_to_p2(&parm[mc][0], (UTINY)0, &wave_l[mc], mc, &new_opt
[mc]);
              t_parm[mc][0] = 0.0;
              t_parm[mc][1] = 0.5;
              t_parm[mc][2] = 1.0;
              return;
              }
          else
              { /* Block B1.b.iijj */
              /* set next parameter */
              for (i = 0; i < NUM_PARM; ++i)
                  parm[mc][i] = save_parm[mc][i];
              t_parm[mc][0] = parm[mc][curr_parm[mc]];
              parm[mc][curr_parm[mc]] += radius[mc] * (range[mc][curr_parm
[mc]][1] - range[mc][curr_parm[mc]][0]);
              rorm_parm(&parm[mc][0]);
              wave_l[mc] = wl_save[mc];   /* restore nominal wl */
              talk_to_p2(&parm[mc][0], (UTINY)0, &wave_l[mc], mc, &new_opt
[mc]);
              return;
              }
          }
      }
  else
      {  /* reps rot done, continue reading. Block B2 */
      talk_to_p2(&parm[mc][0], (UTINY)1, &wave_l[mc], mc, &new_opt[mc]);
      return;
      }
  }

/* parm_scale - check that estimated values are within range
*/
FLOAT parm_scale (opt_p, save_p, range, mc)
    FLOAT opt_p[][NUM_PARM], save_p[][NUM_PARM], range[][NUM_PARM][2];
    FAST UTINY mc;

{
    /* ensure that the value:
    save_p[i] + 2 * (opt_p[i] - save_p[i]) is within range
    for all i's.
    Return a scaling factor that reduces the extrapolation such that
    the above condition will be met.
    */
    FLOAT temp;
    FAST COUNT i;
    FLOAT v_scale = 2.0;    /* reduce if opt_p out of bounds */ for (i = 0; i < NUM_PARM; ++i)
        {
        if (parm_check(range, mc, (UTINY)i) < NUM_PARM)
            {
            temp = v_scale * (opt_p[mc][i] - save_p[mc][i]);
            if (temp > 0.0) /* increase the parameter */
                if (temp + save_p[mc][i] > range[mc][i][1])
                    v_scale = (1.0/v_scale) * (range[mc][i][1] - save_p[mc][i])/
(opt_p[mc][i] - save_p[mc][i]);
            if (temp < 0.0)
                if (temp + save_p[mc][i] < range[mc][i][0])
                    v_scale = (1.0/v_scale) * (range[mc][i][0] - save_p[mc][i])/
(opt_p[mc][i] - save_p[mc][i]);
            }
```

```
        )
    return(v_scale);
    )

/* find_width - measure FWHM (full width at half maximum
 */

FLOAT find_width(d, rdata, imax)
    FLOAT d[];
    COUNT ndata;
    COUNT imax;     /* location of point of maximum intensity */

(
    FAST COUNT i;
    FLOAT xmax, xmin, half_max;
    FLOAT right = ndata - 1, left = 0;
    FLOAT frac_max; /* fractional step number of maximum intensity */ xmax = d[imax];
    xmin = find_min(c, ndata);
    frac_max = max_x(d, imax);  /* interpolate x coord. of max intens */
    half_max = (xmax + xmin)/2.0;
    /* search in neighborhood of maximum for points that vertically
    bracket the half-maximum */
    for (i = imax; i < ndata - 1; ++i)
        if (d[i] >= half_max && d[i + 1] < half_max)
            (
            right = i + (half_max - d[i])/(d[i + 1] - d[i]);
            break;
            )
    for (i = imax; i > 0; --i)
        if (d[i] >= half_max && d[i - 1] < half_max)
            (
            left = i + (half_max - d[i])/(d[i] - d[i - 1]);
            break;
            )
    /* reduce width by 50 for scaling with signal cv's */
    return(.02 * max(right - frac_max, frac_max - left));
    )

/* max_pos - find the index of the highest value in the data buffer
 */
COUNT max_pos(data, rdata)
    FAST FLOAT *data;
    FAST COUNT ndata;

(
    FAST COUNT i;
    FLOAT mx = -1.0e20;     /* large negative number */
    COUNT imax;

for (i = 0; i < rdata; ++i)
        (
        if (*data > mx)
            (
            mx = *data;
            imax = i;
            )
        ++data;
        )
    return(imax);
    )

/* talk_to_p2 - tell p2 to parameters to give to the instrument
 */

VOID talk_to_p2(parm, command, wl, mc, goodness)
    FAST FLOAT *parm;
    FAST UTINY command;
    FLOAT *wl;
    FLOAT *goodness; /* a measure of the performance of current settings */
    UTINY mc;

(
    FAST FILE quel;
    TEXT buffer[24];
    COUNT i;
```

```
    buffer[0] = 'H';
    buffer[1] = 'Z';
    buffer[2] = mc ? 'B' : 'A';
    buffer[3] = command;
    make_buffer(&buffer[4], wl, parm);
    if (command == 2) /* optimize all done */
        *goodness = 1.0/ *goodness:
        buff_append(&buffer[20], goodness); /* append goodness value */
    i = (command == 2) ? 24 : 20;
    quel = open("/dev/quel", WRITE, 0);
    write(quel, buffer, i);
    close(quel);
    return;
    }

/* make_buffer - pack text buffer for transmission to p2
 */
VOID make_buffer(buff, wl, parm)
    FAST TEXT *buff, *wl, *parm;

{
    UTINY i = 4;

while (i--)
        *buff++ = *wl++;
    i = 4 * NUM_PARM;
    while (i--)
        *buff++ = *parm++;
    return;
    }

/* buff_append - append 'goodness' value to the string
 */
VOID buff_append(buffer, goodness)
    FAST TEXT *buffer, *goodness;

{
    FAST COUNT i = 4;
    while (i--)
        *buffer++ = *goodness++;
    return;
    }
/* eval_func - evaluate the spectrum for precision, det, limit and
freedom from interference
 */
FLOAT eval_func(eval_cond, weights)
    FLOAT eval_cond[], weights[];

{
    FAST COUNT i;
    FLOAT value = 0.0; /* evaluation function is the sum of 3 factors*/
    FLOAT sum_weights = 0.0;
    for (i = 0; i < NUM_COND; ++i)
        {
        value += eval_cond[i] * weights[i];
        sum_weights += weights[i];
        }
        value /= sum_weights;
    return (value);
    }

/* parm_check - check for invariant parameters
 */
UTINY parm_check(range, mc, index)
    FLOAT range[][NUM_PARM][2];
    UTINY mc;
    UTINY index;

{
    if (range[mc][index][1] >= 0.0) /* negative upper range implies invariance */
        return(index);
    else
        {
        if (++index >= NUM_PARM)
            return((UTINY)NUM_PARM);    /* no parameters left */
        else
            return(parm_check(range, mc, index));
        }
```

```
            }
#define SMALL 1.0e-10

/* parabola - parabolic interpolation
 */
FLOAT parabola(x, y,xd)

FLOAT x[], y[], *xd;
    {
/* parabola(x,y,&xd)
 *          returns : ly - lowest y-value for computed parabola
 *                  : xd - corresponding x-coordinate
 *                  : defaults to lowest y-input if
 *                  :   1 - 2 x-inputs are equal
 *                  :   2 - computed a = 0.0
 *                  :   3 - d2y/dx2 is negative
 *
 * parabola.c  Fitting parabola to 3 coordinates   Mar. 1984,
 *          revised Apr. 5, 1984 to return minimum y-value
 *  INPUT : [x(i),y(i)] i=1,3   **  all x's must be different ! **
 *  COMPUTES : 1 - a,b,c for y(i)=a*x(i)*x(i)+b*x(i)+c
 *             2 - xd = x when dy/dx=0
 *             3 - sign d2y/dx2
 *             4 - ly = a * xd * xd + b * xd + c
 *                  or defaults to lowest y-input
 *  VARIABLES : 1 - denominators
 *                  d10 = x[1] - x[0]
 *                  d20 = x[2] - x[0]
 *                  d21 = x[2] - x[1]
 *              2 - xd - value of x when f'(x) = 0
 *  written by : Barbara Vidal
 */

FLOAT a, b, c, ly;
    FLOAT d10, d20, d21;
    UTINY i;

d10 = x[1] - x[0];      /* computes denominators */
    d20 = x[2] - x[0];      /* if any equal zero */
    d21 = x[2] - x[1];      /* then must use default values */
    if((abs(d10) && abs(d20) && abs(d21)) >= SMALL)
        {
        a = ((y[2] - y[0]) / d20);       /* computes a, b, c thru */
        a -= ((y[1] - y[0]) / d10);      /* elimination in 3 equations */
        a /= d21;                        /*  a*x*x + b*x + c = y   */
        b = ((y[1] - y[0]) / d10) - a * (x[1] + x[0]);
        c = y[0] - (a * x[0] * x[0]) - b * x[0];

/* find x when dy/dx = 0, dy/dx = 2ax+b, x=-b/2a
         * if a=0.0 : use default value
         */
        if( abs(a) > SMALL )
            {
            *xd = -b / (2.0 * a);

/* check sign of d2y/dx2, if negative : use default value
             */
            if( a > 0.0 )
                {
                ly = a * *xd * *xd + b * *xd + c;
                /* test reasonableness of computed y minimum    */
                    i = ((y[1] < y[0]) ? 1 : 0);
                    i = ((y[2] < y[i]) ? 2 : i);
                    d10 = y[i] - abs(y[i]) / 2.0;
                    if( ly < d10 )
                        {
                        /* use DEFAULT values for ly, xd     */
                        ly = y[i];
                        *xd = x[i];
                        return(ly);
                        }
                /* passed all tests : returns lowest y for parabola
                 */
                return(ly);
                }
            }
        }

/* default values :  ly = lowest y[i] input, xd = x[i]   */
```

```
            i = ((y[1] < y[0]) ? 1 : 0);
            i = ((y[2] < y[i]) ? 2 : i);
            ly = y[i];
            *xd = x[i];
            return(ly);
    }

/* norm_parm - round the values of the parameters s.t. only reasonable
values are requested from p2
 */

VOID norm_parm(parm)
    FLOAT parm[];

{
    FAST LONG i;
    /* set upper and lower limits of parameter values */
    /* add additional limit as parameters are added */
    LOCAL FLOAT u_limit[] = (35.0, 2000.0, 2.0);
    LOCAL FLOAT l_limit[] = ( 0.0,  200.0, 0.0);

for (i = 0; i < NUM_PARM; ++i)
        {
        /* ensure that values are in range of the hardware */
        parm[i] = min(parm[i], u_limit[i]);
        parm[i] = max(parm[i], l_limit[i]);
        }
    i = parm[0] + 0.5;
    parm[0] = i;    /* round height to nearest integer */
    i = (parm[1] + 10.0)/20.0;
    parm[1] = i * 20;   /* round power to nearest 20 watts */
    i = (parm[2] + 0.005) * 100.0;
    parm[2] = i / 100.0;    /* round neb flow to nearest 0.01 units */
    /* add additional parameters here */

/* --------- */
    return;
    }

/* max_x - find fractional step number of position of maximum intensity
 */

FLOAT max_x (d, imax)
    FLOAT d[];
    COUNT imax;
    /* note: imax is required to be neither end of the spectrum
    This must be enforced in the calling routine */

{
    FLOAT y0, y1, y2, x0, x1, x2, a, b;

x0 = imax - 1;
    x1 = imax;
    x2 = imax + 1;
    y0 = d[imax - 1];
    y1 = d[imax];
    y2 = d[imax + 1];
    a = (y0 - 2.0 * y1 + y2) / (x0 * x0 - 2.0 * x1 * x1 + x2 * x2);
    b = a * (x0 * x0 - x1 * x1) + y1 - y0;
    return(-b / (2.0 * a));
    }

/* phase - compute the overlap between two signals
 */

DOUBLE phase(x, y, x2, y2, xy)
    DOUBLE x, y;    /* sums of x and y, respectively */
    DOUBLE x2, y2;  /* sums of x*x and y*y, respectively */
    DOUBLE xy;      /* sum of x*y */

{
    DOUBLE n1, n2;  /* normalization constants */
    DOUBLE k = 1.0 / NUM_READS;
    FLOAT sig_a, sig_r, mean_a, mean_r, r;
    DOUBLE rel_a, rel_r;

/* this routine computes the signal enhancement factor as derived
    by Tracy and Myers
    */
```

```
n1 = sqrt(abs(x2 - K * x * x));
n2 = sqrt(abs(y2 - K * y * y));
r = 1./(n1 * n2) * (xy - K * x * y);
stats(x, x2, (COUNT)NUM_READS, &mean_a, &sig_a);
stats(y, y2, (COUNT)NUM_READS, &mean_r, &sig_r);
rel_a = sig_a/mean_a;
rel_r = sig_r/mean_r;
return (rel_a/sqrt(abs(rel_a*rel_a + rel_r*rel_r - 2.0*r*rel_a*rel_r)));
}
```

COPYRIGHT 1985    THE PERKIN-ELMER CORPORATION
ALL RIGHTS RESERVED

What is claimed is:

1. An apparatus for optimizing a measurement characteristic as a function of a plurality of adjustable parameters on an instrument for analysis of a chemical sample, the apparatus comprising, in combination:

means defining an operating range for each adjustable parameter within which range the setting thereof is to optimize said characteristic;

means for selecting a starting operating point for each adjustable parameter within its defined operating range;

means to measure the characteristic to be optimized at said starting operating point and at a plurality of other operating points where each adjustable parameter is varied one at a time to a value first above and then below the starting operating point but within the operating range, said measurement means producing at least three measurements of the characteristic to be optimized as a function of each adjustable parameter;

means to determine by interpolation of a function having a non-zero second derivative and having points defined by each set of measurements of the characteristic to be optimized as a function of each adjustable parameter the optimum point within the operating range of each adjustable parameter on each curve calculated by interpolation, the optimum point on each said curve comprising one of the operating coordinates of a first test point, the coordinates of said first test point comprising the end of a conjugate vector starting at said starting operating point and ending at said first test point;

means to calculate the coordinates of a second test point which is located at the end of a vector which is twice said conjugate vector;

said means to measure said characteristic to be optimized also being operative to measure the characteristic to be optimized at said first test point and said second test point;

said means to determine by interpolation of said function having a non-zero second derivative being operative to determine the coordinates of a third test point which comprises the optimum point in the operating range of each adjustable parameter on a curve defined by the measurement of said characteristic to be optimized at the values for each adjustable parameter at said start, said first test and said second test points;

said means to measure said characteristic to be optimized being operative at said third test point and at a plurality of operating points where each adjustable parameter is varied one at a time to a value first above and then below the third test point but within the operating range, said measurement means producing at least three additional measurements of said characteristic to be optimized as a function of each adjustable parameter;

said means to determine by interpolation of said function having a non-zero second derivative being operative to determine the optimum point in the operating range for each adjustable parameter on the curve defined by said interpolation of said additional measurements for each adjustable parameter, the optimum point so calculated comprising a fourth test point lying at the end of a second conjugate vector extending from said third test point to said fourth test point;

said means to calculate the coordinates of said second test point being operative to calculate the coordinates of a fifth test point which is located at the end of a vector twice said second conjugate vector; and said means to determine by interpolation of a function having a non-zero second derivative being operative to determine the optimum value of said characteristic to be optimized lying on a curve defined by said third test point, said fourth test point and said fifth test point, the location where said optimum value occurs comprising the optimum point for operating the instrument.

2. The apparatus of claim 1 wherein each adjustable parameter is adjusted by no greater than 20% of the operating range about said starting point.

3. The apparatus of claim 1 where the characteristic to be optimized is the detection limit.

4. The apparatus of claim 1 wherein one adjustable parameter is the nebulizer gas flow rate.

5. The apparatus of claim 4 wherein one adjustable parameter is the power to the induction coil of an inductively coupled plasma spectrometer.

6. The apparatus of claim 5 wherein one adjustable parameter is the viewing height of the monochrometer in an inductively coupled plasma spectrometer.

7. The apparatus of claim 6 wherein the characteristic to be optimized is the detection limit.

8. The apparatus of claim 1 wherein one adjustable parameter is the power to the induction coil of an inductively coupled plasma spectrometer.

9. The apparatus of claim 1 wherein one adjustable parameter is the viewing height of the monochrometer in an inductively coupled plasma spectrometer.

10. The apparatus of claim 1 wherein each adjustable parameter is adjusted by no more than 10% of the operating range about said third test point.

11. A method for optimizing a measurement characteristic as a function of a plurality of adjustable parameters on an instrument for analysis of a chemical sample, the method comprising the steps of:

defining an operating range for each adjustable parameter within which range the setting thereof is to optimize said characteristic;

selecting a starting operating point for each adjustable parameter within its defined operating range;

measuring the characteristic to be optimized at said starting operating point and at least at two other operating points for each adjustable parameter where each adjustable parameter is varied one at a time to a value first above and then below the starting operating point but within the operating range;

determining by interpolation of a function having a non-zero second derivative and having points defined by each set of measurements of the characteristic to be optimized as a function of each adjustable parameter the optimum point within the operating range of each adjustable parameter on each curve calculated by interpolation, the optimum point on each said curve comprising one of the operating coordinates of a first test point, the coordinates of said first test point comprising the end of a conjugate vector starting at said starting operating point and ending at said first test point;

calculating the coordinates of a second test point which is located at the end of a vector which is twice said conjugate vector;

measuring said characteristic to be optimized at said first test point and said second test point;

determining by interpolation of a function having a non-zero second derivative the coordinates of a third test point which comprises the optimum point in the operating range of each adjustable parameter on a curve defined by the measurement of said characteristic to be optimized at the values for each adjustable parameter at said start, said first test and said second test points;

measuring said characteristic to be optimized at said third test point and at a plurality of operating points where each adjustable parameter is varied one at a time to a value first above and then below the third test point but within the operating range, said measurement means producing at least three additional measurements of said characteristic to be optimized as a function of each adjustable parameter;

determining by interpolation of a function having a non-zero second derivative the optimum point in the operating range for each adjustable parameter on the curve defined by said three additional measurements for each adjustable parameter, the optimum point so calculated comprising a fourth test point lying at the end of a second conjugate vector extending from said third test point to said fourth test point;

calculating the coordinates of a fifth test point which is located at the end of a vector twice said second conjugate vector;

determining by interpolation of a function having a non-zero second derivative the optimum value of said characteristic to be optimized lying on a curve defined by said third test point, said fourth test point and said fifth test point, the location where said optimum value occurs comprising the optimum operating point for the instrument, and measuring the characteristic to be optimized at said optimum operating point.

12. The method of claim 11 wherein each adjustable parameter is adjusted by no greater than 20% of the operating range about said starting point.

13. The method of claim 11 where the characteristic to be optimized is the detection limit.

14. The method of claim 11 wherein one adjustable parameter is the nebulizer gas flow rate.

15. The method of claim 14 wherein one adjustable parameter is the power to the induction coil of an inductively coupled plasma spectrometer.

16. The method of claim 15 wherein one adjustable parameter is the viewing height of the monochrometer in an inductively coupled plasma spectrometer.

17. The method of claim 16 wherein the characteristic to be optimized is the detection limit.

18. The method of claim 11 wherein one adjustable parameter is the power to the induction coil of an inductively coupled plasma spectrometer.

19. The method of claim 11 wherein one adjustable parameter is the viewing height of the monochrometer in an inductively coupled plasma spectrometer.

20. The method of claim 11 wherein each adjustable parameter is adjusted by no more than 10% of the operating range about said third test point.

* * * * *